US012731004B2

(12) United States Patent
Lee et al.

(10) Patent No.: US 12,731,004 B2
(45) Date of Patent: Sep. 8, 2026

(54) ELECTRONIC APPARATUS AND CONTROLLING METHOD THEREOF

(71) Applicant: Samsung Electronics Co., Ltd., Suwon-si (KR)

(72) Inventors: Hyunwoo Lee, Suwon-si (KR); Sangyeon Kim, Suwon-si (KR); Jonghee Han, Suwon-si (KR)

(73) Assignee: Samsung Electronics Co., Ltd., Suwon-si (KR)

( * ) Notice: Subject to any disclaimer, the term of this patent is extended or adjusted under 35 U.S.C. 154(b) by 269 days.

(21) Appl. No.: 18/299,355

(22) Filed: Apr. 12, 2023

(65) Prior Publication Data

US 2023/0244913 A1 Aug. 3, 2023

Related U.S. Application Data

(63) Continuation of application No. PCT/KR2022/014987, filed on Oct. 5, 2022.

(30) Foreign Application Priority Data

Oct. 5, 2021 (KR) ........................ 10-2021-0131472
Mar. 10, 2022 (KR) ........................ 10-2022-0030359

(51) Int. Cl.
*G06N 3/04* (2023.01)
*A61B 5/00* (2006.01)
(Continued)

(52) U.S. Cl.
CPC ........... *G06N 3/045* (2023.01); *A61B 5/4818* (2013.01); *G01S 13/62* (2013.01); *G01S 13/88* (2013.01); *G06N 3/09* (2023.01)

(58) Field of Classification Search
CPC ........ G06N 3/045; G06N 3/09; A61B 5/4818; G01S 13/62; G01S 13/88
(Continued)

(56) References Cited

U.S. PATENT DOCUMENTS 11,055,575 B2 * 7/2021 Anushiravani ......... G10L 15/16
2014/0194793 A1 * 7/2014 Nakata .................... G01S 13/87
601/48

(Continued)

FOREIGN PATENT DOCUMENTS

CN 111603138 A 9/2020
CN 112115863 A 12/2020

(Continued)

OTHER PUBLICATIONS

An et al. "Squeeze-and-Excitation on Spatial and Temporal Deep Feature Space for Action Recognition," ,arXiv:1806.00631v2 [cs. CV] Jul. 20, 2018, pp. 1-6 (Year: 2018).*

(Continued)

*Primary Examiner* — Samarina Makhdoom
(74) *Attorney, Agent, or Firm* — Jefferson IP Law, LLP

(57) ABSTRACT

An electronic apparatus is provided. The electronic apparatus includes an ultra-wideband (UWB) sensor, a memory storing at least one instruction, and a processor. The processor, by executing the at least one instruction, is configured to transmit a radar signal through the UWB sensor and receive a signal reflected by a user, acquire first information on the user's movement based on the reflected signal, acquire second information on the user's movement by performing a Fourier transform on the first information, acquire first feature information corresponding to the first information and second feature information corresponding to the second information by inputting the first information and the second information to a first neural network and a second neural network, respectively, acquire information on the user's sleep by inputting the first feature information and the second feature information into a third neural network, and provide information on the acquired sleep.

16 Claims, 15 Drawing Sheets

(51) Int. Cl.

| | |
|---|---|
| ***G01S 13/62*** | (2006.01) |
| ***G01S 13/88*** | (2006.01) |
| ***G06N 3/045*** | (2023.01) |
| ***G06N 3/09*** | (2023.01) |

(58) Field of Classification Search

USPC .......................................................... 342/114

See application file for complete search history.

(56) References Cited

U.S. PATENT DOCUMENTS

| | | | |
|---|---|---|---|
| 2018/0055384 | A1 | 3/2018 | Ambili et al. |
| 2021/0149041 | A1 | 5/2021 | Cho et al. |
| 2022/0313113 | A1 | 10/2022 | Cho et al. |

FOREIGN PATENT DOCUMENTS

| | | | | | |
|---|---|---|---|---|---|
| CN | 108065916 | B | | 4/2021 | |
| CN | 108652601 | B | | 4/2021 | |
| CN | 112716474 | A | * | 4/2021 | ........... A61B 5/0507 |
| CN | 109480787 | B | | 6/2021 | |
| EP | 3835812 | A1 | * | 6/2021 | ......... G01S 13/0209 |
| JP | 2020-503102 | A | | 1/2020 | |
| KR | 10-1866517 | B1 | | 6/2018 | |
| KR | 10-2134154 | B1 | | 7/2020 | |
| KR | 10-2021-0009822 | A | | 1/2021 | |
| KR | 10-2236420 | B1 | | 4/2021 | |
| KR | 10-2021-0063004 | A | | 6/2021 | |
| KR | 10-2266555 | B1 | | 6/2021 | |
| KR | 10-2021-0090373 | A | | 7/2021 | |
| WO | WO-2019079855 | A1 | * | 5/2019 | ........... A61B 5/0806 |

OTHER PUBLICATIONS

Tsai et al. "Multimodal Transformer for Unaligned Multimodal Language Sequences," arXiv:1906.00295v1 [cs.CL] Jun. 1, 2019 (Year: 2019).*

Zhou et al. "Validation of Novel Automatic Ultra-wideband Radar for Sleep Apnea Detection," J Thorac Dis. Apr. 2020;12(4):1286-1295. doi: 10.21037/jtd.2020.02.59 (Year: 2020).*

Kang et al., "Non-contact diagnosis of obstructive sleep apnea using impulse-radio ultra-wideband radar," Scientific Reports, 2020.

Kwon et al., "Hybrid CNN-LSTM Network for Real-Time Apnea-Hypopnea Event Detection Based on IR-UWB Radar," IEEE access, 2021.

International Search Report and written opinion dated Jan. 26, 2023, issued in International Application No. PCT/KR2022/014987.

Extended European Search Report dated on Jan. 21, 2025, issued in European Application No. 22878883.2-1113.

European Examination Report dated Aug. 5, 2025, issued in European Application No. 22878883.2.

Indian Examination Report dated Nov. 12, 2025, issued in Indian Application No. 202427027264.

European Summons to attend oral proceedings dated Mar. 11, 2026, issued in European Application No. 22878883.2.

* cited by examiner

FIG. 7

| | INPUT DATA | MEASUREMENT TIME | NEURAL NETWORK STRUCTURE | COMBINING METHOD | ACCURACY | SENSITIVITY | SPECIFICITY |
|---|---|---|---|---|---|---|---|
| 710 | FIRST INFORMATION | 10 MINUTES | 1DCNN-LSTM | | 0.785 | 0.659 | 0.831 |
| 720 | FIRST INFORMATION | 60 MINUTES | 1DCNN-LSTM | | 0.817 | 0.733 | 0.834 |
| 730 | SECOND INFORMATION | 60 MINUTES | 1DCNN-LSTM | | 0.891 | 0.78 | 0.94 |
| 740 | FIRST INFORMATION + SECOND INFORMATION | 60 MINUTES | TWO STREAM 1DCNN-LSTM | CONCATENATION | 0.907 | 0.816 | 0.942 |
| 750 | FIRST INFORMATION + SECOND INFORMATION | 60 MINUTES | TWO STREAM 1DCNN-SENET-TRANSFORMER | CONCATENATION | 0.927 | 0.902 | 0.939 |
| 760 | FIRST INFORMATION + SECOND INFORMATION | 60 MINUTES | TWO STREAM 1DCNN-SENET-TRANSFORMER | ELEMENT-WISE MULTIPLY | 0.929 | 0.917 | 0.933 |
| 770 | FIRST INFORMATION + SECOND INFORMATION | 60 MINUTES | TWO STREAM 1DCNN-SENET-TRANSFORMER | BIFPN | 0.926 | 0.877 | 0.946 |

ELECTRONIC APPARATUS AND CONTROLLING METHOD THEREOF

CROSS-REFERENCE TO RELATED APPLICATION(S)

This application is a continuation application, claiming priority under § 365(c), of an International application No. PCT/KR2022/014987, filed on Oct. 5, 2022, which is based on and claims the benefit of a Korean patent application number 10-2021-0131472, filed on Oct. 5, 2021, in the Korean Intellectual Property Office, and of a Korean patent application number 10-2022-0030359, filed on Mar. 10, 2022, in the Korean Intellectual Property Office, the disclosure of each of which is incorporated by reference herein in its entirety.

TECHNICAL FIELD

The disclosure relates to an electronic apparatus for identifying apnea or hypopnea during sleep of a user using an ultra-wideband (UWB) signal and a method of controlling thereof.

BACKGROUND ART

With respect to an artificial intelligence model that identifies apnea or hypopnea during sleep of the user by using labeled sleep data (e.g., data on a movement of the user's chest in which an apnea interval or a hypopnea interval is labeled) as learning data, the labeling of the learning data is performed manually. Accordingly, there is a problem in that a matching rate of labeling of the same learning data is different depending on a labeler. In addition, there is a problem in that a performance of the artificial intelligence model is deteriorated according to a deviation of the labeling.

In addition, there is a problem in the related art in that a performance of the artificial intelligence model for identifying apnea or hypopnea during sleep of the user is deteriorated as the user moves while sleep data is measured from the user.

In addition, there is a problem in that the performance of the artificial intelligence model for identifying apnea or hypopnea during sleep of the user is deteriorated even depending on a difference between the environment in which learning data is acquired and the environment in which test data is acquired.

In addition, there is a problem in that the performance of the artificial intelligence model for identifying apnea or hypopnea during sleep of the user is deteriorated even depending on a difference between a user in which learning data is acquired and a user in which test data is acquired (e.g., difference in movement change during sleep).

The above information is presented as background information only to assist with an understanding of the disclosure. No determination has been made, and no assertion is made, as to whether any of the above might be applicable as prior art with regard to the disclosure.

TECHNICAL SOLUTION

Aspects of the disclosure are to address at least the above-mentioned problems and/or disadvantages and to provide at least the advantages described below. Accordingly, an aspect of the disclosure is to provide an electronic apparatus that acquires information on the user's sleep by using an artificial intelligence model learned based on information on a change in the user's movement during sleep and information on a change in a frequency of a user's movement during sleep, and a controlling method thereof.

Additional aspects will be set forth in part in the description which follows and, in part, will be apparent from the description, or may be learned by practice of the presented embodiments.

In accordance with an aspect of the disclosure, an electronic apparatus is provided. The electronic apparatus includes an ultra-wideband (UWB) sensor, a memory configured to store at least one instruction, and a processor configured to be connected to the memory and control the electronic apparatus, wherein the processor is configured to, by executing the at least one instruction, transmit a radar signal through the UWB sensor and receive a signal reflected by a user, acquire first information on the user's movement based on the reflected signal, acquire second information on the user's movement by performing a Fourier transform on the first information, acquire first feature information corresponding to the first information and second feature information corresponding to the second information by inputting the first information and the second information to a first neural network and a second neural network, respectively, acquire information on the user's sleep by inputting the first feature information and the second feature information into a third neural network, and provide information on the acquired sleep.

The processor may acquire information on the user's sleep by inputting a value acquired by multiplying the first feature information and the second feature information for each element into the third neural network.

The first information may be a distance map with respect to a movement of the user's chest, and wherein the second information is a Doppler map with respect to the movement of the user's chest.

The first information may be time series information on the user's movement according to a change of time, and wherein the second information is time series information on a frequency of the user's movement according to the change of time.

The first neural network may include a convolutional neural network (CNN) for outputting the first feature information, and wherein the processor is configured to acquire restored first information using the acquired first feature information, and train parameters of the CNN by comparing the restored first information with the acquired first information.

The second neural network may include a convolutional neural network (CNN) for outputting the second feature information, and wherein the processor is configured to acquire restored second information by using the acquired second feature information, and train parameters of the CNN by comparing the restored second information with the acquired second information.

The first neural network, the second neural network, and the third neural network may be trained based on information on the user's movement measured over a predetermined time.

In accordance with another aspect of the disclosure, a method of controlling an electronic apparatus is provided. The method includes transmitting a radar signal through UWB sensor and receiving a signal reflected by the user, acquiring first information on the user's movement based on the reflected signal, acquiring second information on the user's movement by performing a Fourier transform on the first information, acquiring first feature information corresponding to the first information and second feature information corresponding to the second information by inputting the first information and the second information to a first neural network and a second neural network, respectively, acquiring information on the user's sleep by inputting the first feature information and the second feature information into a third neural network, and providing information on the acquired sleep.

The acquiring information on the user's sleep may include acquiring information on the user's sleep by inputting a value acquired by multiplying the first feature information and the second feature information for each element into the third neural network.

The first information may be a distance map with respect to a movement of the user's chest, and wherein the second information is a Doppler map with respect to the movement of the user's chest.

The first information may be time series information on the user's movement according to a change of time, and wherein the second information is time series information on a frequency of the user's movement according to the change of time.

The first neural network may include a convolutional neural network (CNN) for outputting the first feature information, and wherein the method further includes acquiring restored first information using the acquired first feature information, and training parameters of the CNN by comparing the restored first information with the acquired first information.

The second neural network may include a convolutional neural network (CNN) for outputting the second feature information, and wherein the method further includes acquiring restored second information by using the acquired second information feature information, and training parameters of the CNN by comparing the restored second information with the acquired second information.

The first neural network, the second neural network, and the third neural network may be trained based on information on the user's movement measured over a predetermined time.

In accordance with another aspect of the disclosure, a non-transitory computer-readable recording medium including a program for executing a control method of an electronic apparatus is provided. The control method includes transmitting a radar signal through UWB sensor and receiving a signal reflected by the user, acquiring first information on the user's movement based on the reflected signal, acquiring second information on the user's movement by performing a Fourier transform on the first information, acquiring first feature information corresponding to the first information and second feature information corresponding to the second information by inputting the first information and the second information to a first neural network and a second neural network, respectively, acquiring information on the user's sleep by inputting the first feature information and the second feature information into a third neural network, and providing information on the acquired sleep.

Through the above-described embodiments, the electronic apparatus has an effect of accurately identifying the user's apnea or hypopnea during sleep.

Other aspects, advantages, and salient features of the disclosure will become apparent to those skilled in the art from the following detailed description, which, taken in conjunction with the annexed drawings, discloses various embodiments of the disclosure.

BRIEF DESCRIPTION OF DRAWINGS

The above and other aspects, features, and advantages of certain embodiments of the disclosure will be more apparent from the following description taken in conjunction with the accompanying drawings, in which:

FIG. 7 is a view illustrating a performance of an artificial intelligence model according to an embodiment of the disclosure;

The same reference numerals are used to represent the same elements throughout the drawings.

MODE FOR IMPLEMENTING THE DISCLOSURE

Figure 1:
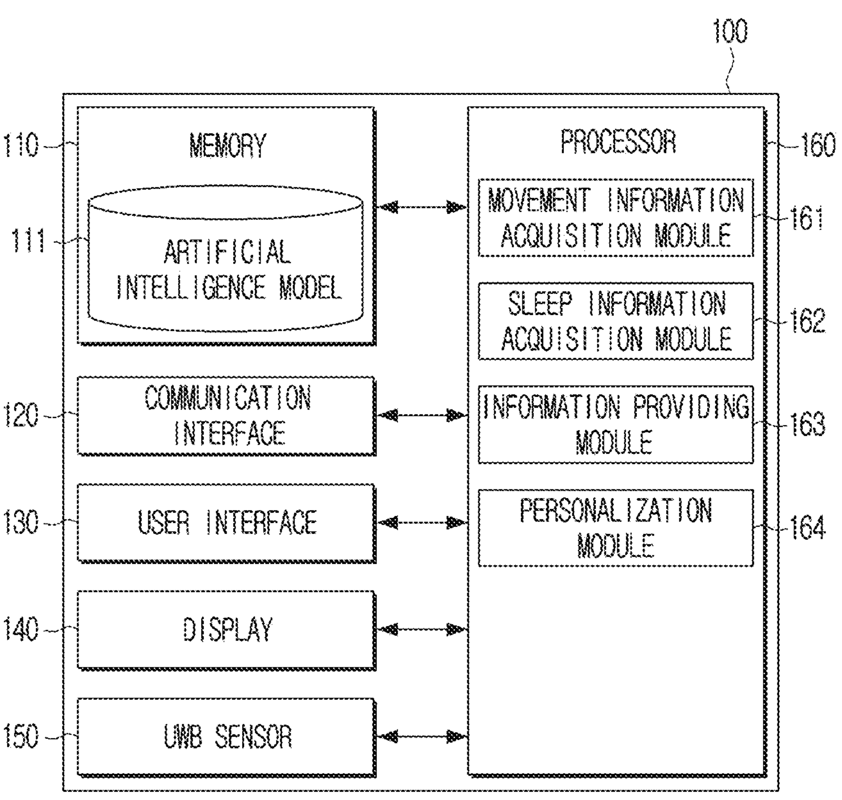
FIG. 1 is a block diagram illustrating a configuration of an electronic apparatus according to an embodiment of the disclosure.

The following description with reference to accompanying drawings is provided to assist in a comprehensive understanding of various embodiments of the disclosure as defined by the claims and their equivalents. It includes various specific details to assist in that understanding but these are to be regarded as merely exemplary. Accordingly, those of ordinary skill in the art will recognize that various changes and modifications of the various embodiments described herein can be made without departing from the scope and spirit of the disclosure. In addition, descriptions of well-known functions and constructions may be omitted for clarity and conciseness.

In addition, the following embodiments may be modified in various other forms, and the scope of the technical spirit of the disclosure is not limited to the following embodiments. Rather, these embodiments are provided to more fully and complete the disclosure, and to fully convey the technical spirit of the disclosure to those skilled in the art.

The terms and words used in the following description and claims are not limited to the bibliographical meanings, but, are merely used by the inventor to enable a clear and consistent understanding of the disclosure. Accordingly, it should be apparent to those skilled in the art that the following description of various embodiments of the disclosure is provided for illustration purpose only and not for the purpose of limiting the disclosure as defined by the appended claims and their equivalents.

It is to be understood that the singular forms "a," "an," and "the" include plural referents unless the context clearly dictates otherwise. Thus, for example, reference to "a component surface" includes reference to one or more of such surfaces.

Singular forms are intended to include plural forms unless the context clearly indicates otherwise.

In the disclosure, the terms "include," "may include," "comprise," or "may comprise" designate the presence of features, numbers, steps, operations, components, elements, or a combination thereof that are written in the specification, but do not exclude the presence or possibility of addition of one or more other features, numbers, steps, operations, components, elements, or a combination thereof.

In the description, the term "A or B," "at least one of A and/or B," or "one or more of A and/or B" may include all possible combinations of the items that are enumerated together. For example, the term "A or B" or "at least one of A or/and B" may designate (1) at least one A, (2) at least one B, or (3) both at least one A and at least one B.

The expression "1," "2," "first," or "second" as used herein may modify a variety of elements, irrespective of order and/or importance thereof, and to distinguish one element from another, without limiting the corresponding elements.

When an element (e.g., a first element) is "operatively or communicatively coupled with/to" or "connected to" another element (e.g., a second element), an element may be directly coupled with another element or may be coupled through the other element (e.g., a third element).

Meanwhile, when an element (e.g., a first element) is "directly coupled with/to" or "directly connected to" another element (e.g., a second element), an element (e.g., a third element) may not be provided between the other element.

In the description, the term "configured to" may be changed to, for example, "suitable for," "having the capacity to," "designed to," "adapted to," "made to," or "capable of" under certain circumstances. The term "configured to (set to)" does not necessarily mean "specifically designed to" in a hardware level.

Under certain circumstances, the term "device configured to" may refer to "device capable of" doing something together with another device or components. For example, a phrase "a sub-processor configured to (set to) perform A, B, and C" may refer to a generic-purpose processor (e.g., central processing unit (CPU) or application processor) capable of performing corresponding operations by executing a dedicated processor (e.g., embedded processor) for performing corresponding operation, or executing one or more software programs stored in a memory device.

In the embodiments disclosed herein, a term 'module' or 'unit' refers to an element that performs at least one function or operation. The 'module' or 'unit' may be realized as hardware, software, or combinations thereof. In addition, a plurality of 'modules' or a plurality of 'units' may be integrated into at least one module and may be at least one processor except for 'modules' or 'units' that should be realized in a specific hardware.

Meanwhile, various elements and areas in the drawings are schematically drawn. Accordingly, the technical spirit of the disclosure is not limited by a relative size or spacing illustrated in the accompanying drawings.

The example embodiments of the disclosure will be described in greater detail below in a manner that will be understood by one of ordinary skill in the art.

FIG. 1 is a block diagram illustrating a configuration of an electronic apparatus according to an embodiment of the disclosure.

Referring to FIG. 1, an electronic apparatus 100 may include a memory 110, a communication interface 120, a user interface 130, a display 140, a UWB sensor 150, and a processor 160. At least some elements of the electronic apparatus 100 may be omitted, and may further include other elements.

In addition, the electronic apparatus 100 may be implemented as a smartphone, but this is only an embodiment, and may be implemented in various forms, such as a tablet personal computer (PC), PC, server, smart television (TV), mobile phone, personal digital assistant (PDA), laptop, media player, e-book a terminal, a digital broadcasting terminal, a navigation system, a kiosk, moving picture experts group layer-3 (MP3) player, a digital camera, a wearable device, a home appliance, and other mobile or non-mobile computing devices.

At least one instruction related to the electronic apparatus 100 may be stored in the memory 110. An operating system (O/S) for driving the electronic apparatus 100 may be stored in the memory 110. In addition, various software programs or applications for operating the electronic apparatus 100 according to various embodiments of the disclosure may be stored in the memory 110. In addition, the memory 110 may include a semiconductor memory such as a flash memory or a magnetic storage medium such as a hard disk, or the like.

Specifically, various software modules for operating the electronic apparatus 100 may be stored in the memory 110 according to various embodiments of the disclosure, and the processor 160 may execute various software modules stored in the memory 110 to control the operation of the electronic apparatus 100. In other words, the memory 110 may be accessed by the processor 160 and perform readout, recording, correction, deletion, update, or the like, on data by the processor 160.

Meanwhile, in the disclosure, the term memory may include a memory 110, a read only memory (ROM) (not shown) in the processor 160, a random access memory (RAM) (not shown), or a memory card (not shown) mounted in the electronic apparatus 100 (e.g., micro secure digital (SD) card, memory stick).

In addition, the memory 110 may store at least one artificial intelligence model 111. The artificial intelligence model 111 may be a learned model that outputs information on the user's sleep when first information on the user's movement and second information on the user's movement are input.

Meanwhile, the user's movement in the disclosure may refer to information including the user's chest movement during sleep. In addition, the first information on the user's movement may be time series information on the user's movement according to time (i.e., information on a change in the user's movement).

FIGS. 2A to 2D are views illustrating input data and learning data of an artificial intelligence model according to various embodiments of the disclosure.

Figure 2A:
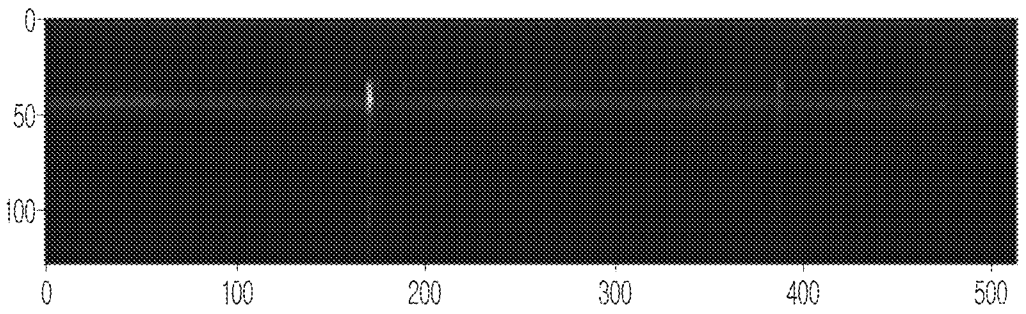
FIGS. 2A, 2B, 2C, and 2D are views illustrating input data and learning data of an artificial intelligence model according to various embodiments of the disclosure.

Referring to FIG. 2A, the first information may be implemented in a form of a distance map. In that configuration, a horizontal axis of the distance map may indicate time, and a vertical axis may indicate a distance from the sensor to a point where a movement is detected.

In addition, second information on the user's movement may be time-series information on a frequency of the user's movement according to time (i.e., information on a change in the frequency of the user's movement).

Figure 2B:
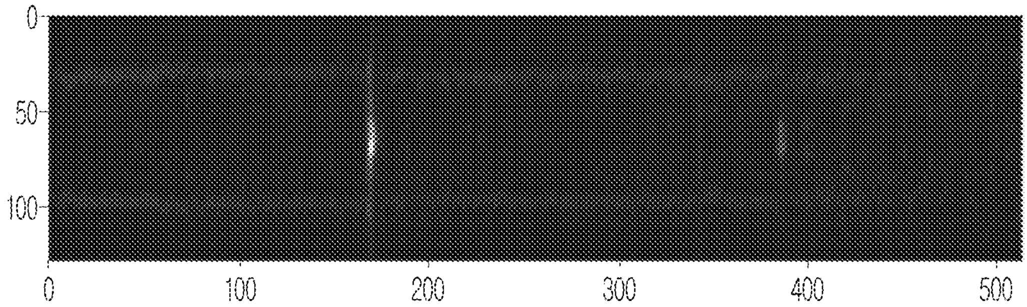

Referring to FIG. 2B, the second information may be implemented as a Doppler map or a micro-Doppler spectrogram. In that configuration, a horizontal axis of the Doppler map may indicate time, and a vertical axis may indicate a frequency of the detected movement.

Meanwhile, the first information is easy to understand information on the distance from the electronic apparatus 100 to the user, but there is a problem in that noise is easily generated according to the user's movement (movement not related to breathing during sleep). In other words, it may be difficult to distinguish between information on a movement related to the user's breathing during sleep (e.g., information on a movement of a chest) and information on a movement related to the user's breathing during sleep. Accordingly, when the artificial intelligence model 111 identifies information on the user's breathing during sleep using only the first information, an accuracy of the artificial intelligence model 111 may be lowered.

Meanwhile, the second information is information on a frequency of the user's movement, and has an advantage in that noise according to the user's movement is small. Accordingly, when the second information is used, there is an effect of accurately analyzing the user's movement.

However, if the user's movement is analyzed using only the second information, there may be a problem in that it is difficult to distinguish a movement of an object or the user in a similar frequency band.

For example, the electronic apparatus 100 may detect not only the user's movement but also a movement of an object (e.g., a fan) around the user. In that configuration, when the frequency of the user's movement and the frequency of the object's movement are similar, it may be difficult to distinguish between the information on the user's movement and the information on the object's movement. In other words, it may be difficult to distinguish between the information on the user's movement and the information on the object's movement. Accordingly, when the artificial intelligence model 111 identifies information on the user's breathing during sleep using only the second information, the accuracy of the artificial intelligence model 111 may be lowered.

Accordingly, when the artificial intelligence model 111 receives the first information and the second information together and identifies the information on the user's breathing during sleep, there may be an effect of minimizing an effect of noise caused by the user's movement during sleep and a noise caused by the movement of an object having a similar frequency to the user's movement, and accurately understanding information on the user's sleep by analyzing information on movement related to breathing during sleep.

Meanwhile, the information on the user's sleep may be information on the user's breathing during sleep (e.g., information on apnea or hypopnea). Specifically, the information on sleep may be information on time, number of occurrences, and the like of apnea or hypopnea that occurred during sleep.

For example, the information on apnea or hypopnea may be an Apnea-Hypopnea Index (AHI). Here, the apnea-hypopnea index represents a sum of the number of occurrences of apnea and hypopnea occurring per hour of sleep, and may be an index for identifying a severity of sleep apnea.

Alternatively, the information on apnea or hypopnea may be whether the apnea-hypopnea index is above or below a specific value.

The artificial intelligence model 111 may be learned based on first information on a movement of the user during sleep and second information on a frequency of a movement of the user during sleep. In that configuration, the first information and the second information may be information labeled as information on apnea or hypopnea during sleep. The labeling may be implemented in various forms such a period in which apnea or hypopnea occurred during the time during which the first information and the second information are measured, time of onset of apnea or hypopnea, number of occurrences of apnea or hypopnea, time duration of apnea or hypopnea, apnea-hypoventilation index, whether the apnea-hypopnea index is above or below a certain value, or the like.

In other words, the artificial intelligence model 111 may be a model that learned a correlation between the first information on the movement of the user and the second information on the frequency of the user's movement and the information on the user's apnea or hypopnea during sleep.

Figure 2C:
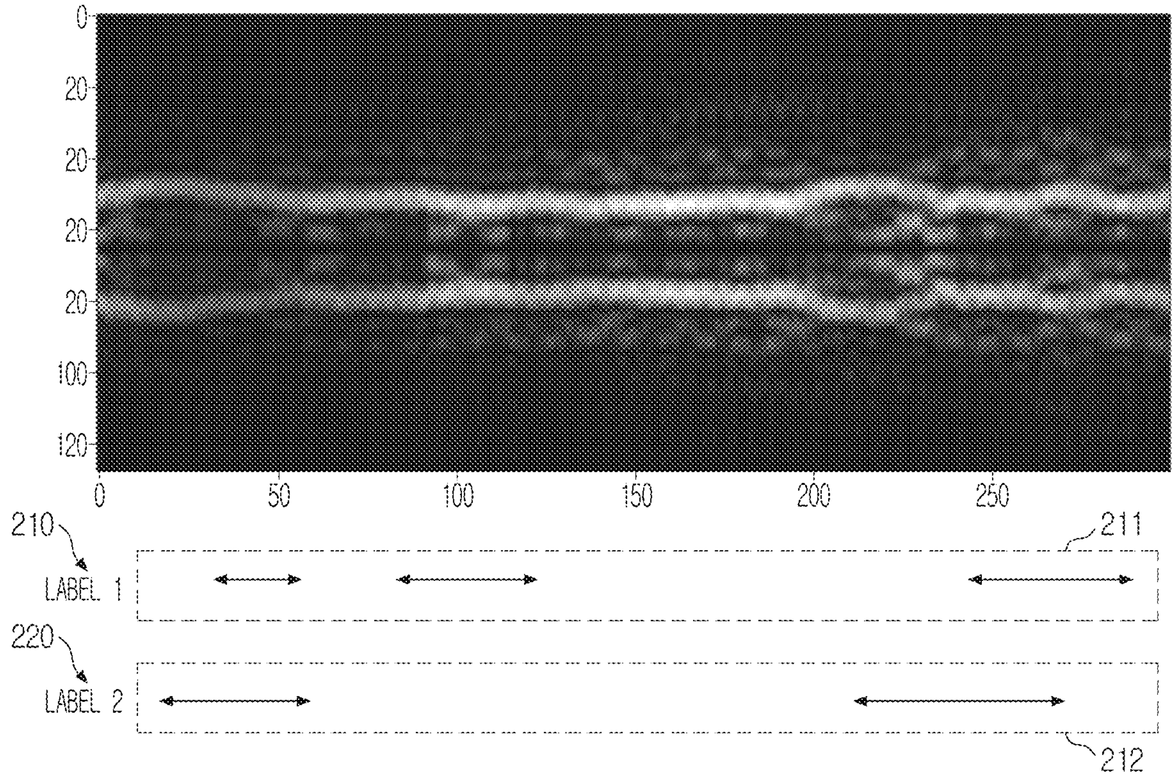

Meanwhile, labeling of learning data may be performed manually by a labeler, and labeling noise may occur in that configuration. FIG. 2C may be a Doppler map indicating a frequency of the user's movement during sleep measured for a predetermined time. In that configuration, the Doppler map may be labeled as an apnea or hypopnea interval during sleep by a labeler.

Referring to FIG. 2C, apnea or hypopnea interval 211 during sleep may be labeled by a first labeler as Label 1 210, and apnea or hypopnea during sleep interval 212 during sleep may be labeled by a second labeler as Label 2 220.

Referring to FIGS. 2A to 2D, the same movement data may be labeled differently depending on the labeler, and accordingly, a labeling error may occur and a performance of the artificial intelligence model 111 may deteriorate.

In order to solve the problem described above, the artificial intelligence model 111 may be learned based on information on the user's movement for which a measurement time is equal to or greater than a predetermined time. In addition, the artificial intelligence model 111 may be a model learned by using information on the user's movement as an independent variable and the number of times of apnea or hypopnea of the user as a dependent variable.

In that configuration, a predetermined time may be identified based on a similarity score between information on movement of a plurality of users labeled by a plurality of labelers. Specifically, a similarity score may be identified between first data in which the apnea or hypopnea interval is labeled by the first labeler and second data in which the apnea or hypopnea interval is labeled by the second labeler for information on the same user's movement.

In this configuration, information on the number of occurrences of apnea or hypopnea may be identified from the first data and the second data. Alternatively, the number of occurrences of apnea or hypopnea may be labeled by the first labeler with respect to information on the same user's movement, and the number of occurrences of apnea or hypopnea may be labeled by the second labeler.

In addition, the similarity score may be a score indicating a similarity between the number of apnea or hypopnea identified in the first data and the number of apnea or hypopnea identified in the second data.

Figure 2D:
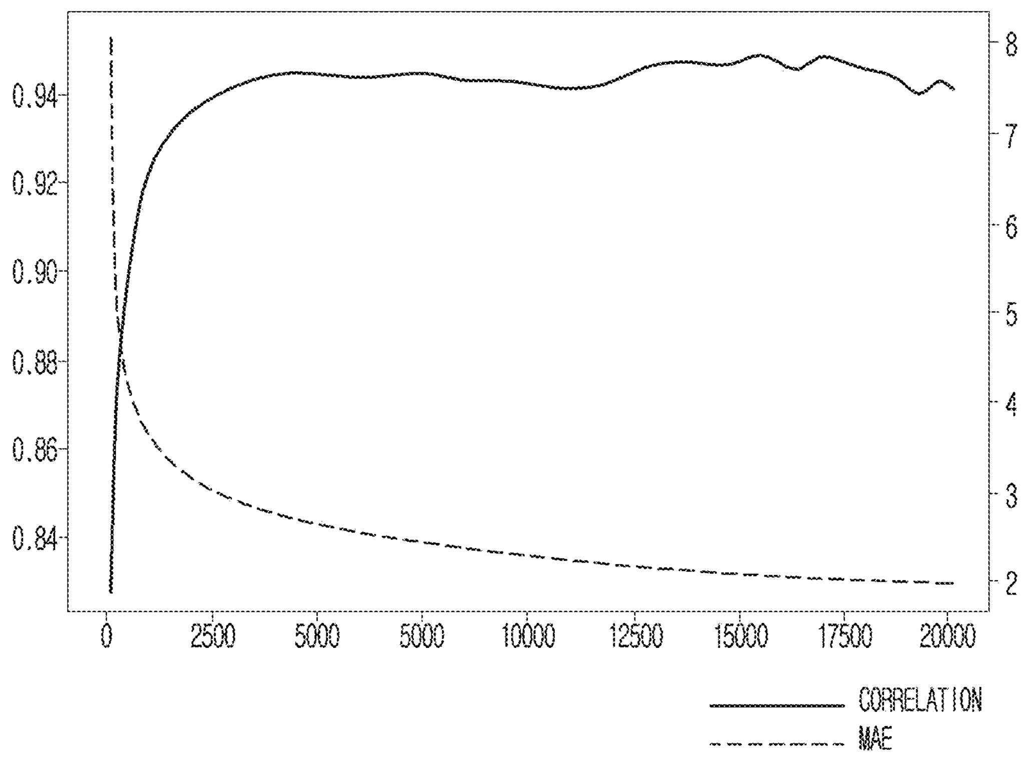

Specifically, referring to FIG. 2D, the similarity score may refer to a correlation or mean absolute error (MAE) between the number of apnea or hypopnea of the first data and the number of apnea or hypopnea of the second data. In that configuration, as the number of apnea or hypopnea identified in the first data is similar to the number of apnea or hypopnea identified in the second data, a correlation value may be higher or a MAE value may be lower. In addition, the similarity score between the first data and the second data may vary according to the measurement time of the data as shown in FIG. 2B. In that configuration, the correlation value may increase or converge as the measurement time increases. Likewise, the MAE value may decrease or converge as the measurement time increases.

Accordingly, based on a comparison result of the similarity score and a threshold value, the predetermined time may be identified. For example, referring to FIG. 2B, when the threshold value is 0.94 and the measurement time is 3600 seconds (1 hour), the correlation may be 0.94 or more. In that configuration, the predetermined time may be identified as 1 hour. Alternatively, when the threshold value is 0.85 and the measurement time is 3600 seconds (1 hour), the MAE value may be 0.85 or less. In that configuration, the predetermined time may be identified as 1 hour.

In other words, as the artificial intelligence model 111 is learned based on the information on the movement measured over a predetermined time (or time interval), a labeling error may be minimized, and the performance of the artificial intelligence model 111 may be improved.

Meanwhile, the artificial intelligence model 111 may include at least one artificial neural network, and the artificial neural network may consist of a plurality of layers. Each of the plurality of neural network layers may have a plurality of weight values, and perform a neural network operation through an operation result of a previous layer and a plurality of weights. The plurality of weights of the plurality of neural network layers may be optimized by the learning result of the artificial intelligence model. For example, the plurality of weights may be updated to reduce or minimize a loss value or a cost value acquired from the artificial intelligence model during the learning process. Here, the weight of each of the layers may be referred to as a parameter of each of the layers.

The artificial neural network may include at least one of various types of neural network models such as Convolution Neural Network (CNN), 1-Dimension Convolution Neural Network (1DCNN), Region with Convolution Neural Network (R-CNN), Region Proposal Network (RPN), Recurrent Neural Network (RNN), Stacking-based deep Neural Network (S-DNN), State-Space Dynamic Neural Network (S-SDNN), Deconvolution Network, Deep Belief Network (DBN), Restricted Boltzman Machine (RBM), Fully Convolutional Network, Long Short-Term Memory (LSTM) Network, Bidirectional-Long Short-Term Memory (Bi-LSTM) Network Classification Network, Plain Residual Network, Dense Network, Hierarchical Pyramid Network, Fully Convolutional Network, Squeeze and Excitation Network (SENet), Transformer Network, Encoder, Decoder, an auto encoder, or a combination thereof, and the artificial neural network in the disclosure is not limited to the above-described example.

Specifically, the artificial intelligence model 111 may include a first neural network that outputs first feature information corresponding to the first information when first information on the user's movement is input, and a second neural network that outputs second feature information corresponding to the second information when second information on the user's movement is input, and a third neural network that outputs information on the user's sleep when the first feature information and the second feature information are input.

Meanwhile, in the disclosure, the first feature information and the second feature information may be implemented in the form of a feature map, but this is only an example and may be implemented in various forms such as a feature vector.

In addition, the first neural network may be learned based on first information on the user's movement, and the second neural network may be learned based on the second information.

In this configuration, the third neural network may be learned based on the first feature information corresponding to the first information on the user's movement, the second feature information corresponding to the second information on the user's movement, and information on the user's sleep (apnea or hypopnea).

In addition, the artificial intelligence model 111 may be learned by an external device in the same manner as described above and stored in the memory 110, but this is only an example, and the artificial intelligence model 111 may be learned by the electronic apparatus 100 and the electronic apparatus may be stored in the memory 110.

The communication interface 120 includes circuitry and is an element capable of communicating with an external device and a server. The communication interface 120 may communicate with an external device and a server based on a wired or wireless communication method. In that configuration, the communication interface 120 may include a Wi-Fi module (not shown), a Bluetooth™ module (not shown), an infrared (IR) module, a local area network (LAN) module, an Ethernet module, or the like. Here, each communication module may be implemented in the form of at least one hardware chip. In addition to the above-described communication methods, the wireless communication module may include at least one communication chip that performs communication according to various wireless communication standards such as ZigBee, universal serial bus (USB), mobile industry processor interface camera serial interface (MIPI CSI), 3rd generation (3G), 3rd generation partnership project (3GPP), long term evolution (LTE), LTE advanced (LTE-A), 4th generation (4G), 5th generation (5G), or the like. However, this is only an embodiment, and the communication interface 120 may use at least one communication module among various communication modules.

The user interface 130 is configured to receive a user command for controlling the electronic apparatus 100. The user interface 130 may be implemented to be device such as button, touch pad, mouse and keyboard, or may be implemented to be touch screen that can also perform the function of the display. The button may include various types of buttons, such as a mechanical button, a touch pad, a wheel, etc., which are formed on the front, side, or rear of the exterior of a main body. The electronic apparatus 100 may acquire various user inputs through the user interface 130. The electronic apparatus 100 may identify that the user is in a sleeping state through a user input input through the user interface 130. Alternatively, the electronic apparatus 100 may identify that the user is in a sleeping state when no user input is input for a threshold period of time or more.

The display 140 may be implemented as a display including a self-luminous element or a display including a non-light-emitting device and a backlight. For example, it may be implemented in various types of displays such as liquid crystal display (LCD), organic light emitting diodes (OLED) displays, light emitting diodes (LED), micro LED, Mini LED, plasma display panel (PDP), quantum dot (QD) displays, quantum dot light-emitting diodes (QLEDs), or the like. In the display 140, a driving circuit, a backlight unit, or the like, which may be implemented in the form of an a-si TFT, a low temperature poly silicon (LTPS) TFT, an organic TFT (OTFT), or the like may also be included. Particularly, the display 140 may display information on the user's sleep.

The UWB sensor 150 may be a sensor for detecting a movement of an object around the electronic apparatus 100 using a UWB signal. Here, the movement of the object may be a movement of the user during sleep. And, the movement of the object may mean a change in a distance from the UWB sensor 150 to the object.

Specifically, the UWB sensor 150 may be implemented as an impulse-radio ultra wideband (IR-UWB) radar sensor. An IR-UWB radar sensor may identify a distance from the UWB sensor 150 to the object or a position of the object by emitting an ultra-wideband impulse signal to the object and measuring time until the signal reflected from the object is received. In other words, the UWB sensor 150 may be a radar sensor that transmits a signal using a wide frequency bandwidth (e.g., 7500 Mhz, etc.) with low power and receives a reflected signal to measure the position of an object. In that configuration, the IR-UWB radar sensor may detect even a minute change in movement, and thus may be used to measure a movement of the user's chest, the user's respiration, or a heart rate of the user.

Meanwhile, in the disclosure, the user's movement may be detected through the UWB sensor 150, but this is only an example, and the user's movement may be detected through various sensors, such as a distance sensor, a lidar sensor, or the like, for detecting the user's movement.

The processor 160 may control overall operations and functions of the electronic apparatus 100. Specifically, the processor 160 is connected to the configuration of the electronic apparatus 100 including the memory 110, and control the overall operation of the electronic apparatus by executing at least one command stored in the memory 110 as described above.

The processor 160 may be implemented in various ways. For example, the processor 160 may be implemented as at least one of an application specific integrated circuit (ASIC), an embedded processor, a microprocessor, hardware control logic, a hardware finite state machine (FSM), or a digital signal processor (DSP). Meanwhile, in the disclosure, the term processor may be used to include a central processing unit (CPU), a graphic processing unit (GPU), a main processing unit (MPU), or the like.

The operation of the processor 160 for implementing various embodiments of the disclosure may be implemented through the artificial intelligence model 111 and a plurality of modules.

Specifically, data for the artificial intelligence model 111 and the plurality of modules according to the disclosure may be stored in the memory 110, and the processor 160 may implement various embodiments according to the disclosure by using the artificial intelligence model 111 and the plurality of modules after accessing the memory 110 and loading the data for the artificial intelligence model 111 and the plurality of modules into the memory or buffer inside the processor 160. In that configuration, the plurality of modules may include a movement information acquisition module 161, a sleep information acquisition module 162, an information providing module 163, and a personalization module 164.

However, at least one of the artificial intelligence model 111 and the plurality of modules according to the disclosure may be implemented as hardware and included in the processor 160 in the form of a system on chip.

A detailed operation of the processor 160 will be described in detail with reference to FIG. 3.

Figure 3:
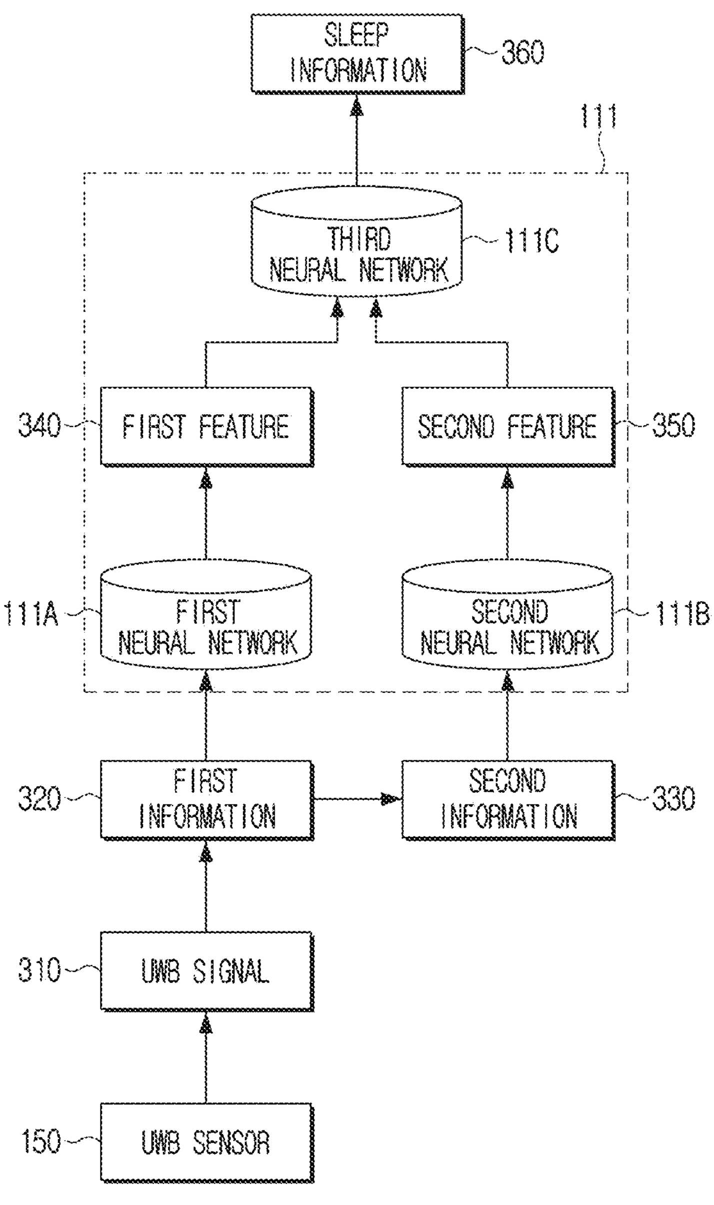
FIG. 3 is a view illustrating an operation of an electronic apparatus according to an embodiment of the disclosure.

FIG. 3 is a view illustrating an operation of an electronic apparatus according to an embodiment of the disclosure.

Referring to FIG. 3, the movement information acquisition module 161 may acquire a UWB signal 310 through the UWB sensor 150 and acquire first information 320 on the user's movement.

Meanwhile, when it is identified that the user is sleeping, the movement information acquisition module 161 may acquire the first information 320 on the user's movement. Specifically, when an input through the user interface 130 is not detected for more than a specific time, the movement information acquisition module 161 may identify that the user is sleeping, and acquire the first information 320 on the user's movement during sleep.

In addition, the movement information acquisition module 161 may acquire second information 330 by performing a Fourier transform on the first information 320.

Figure 4A:
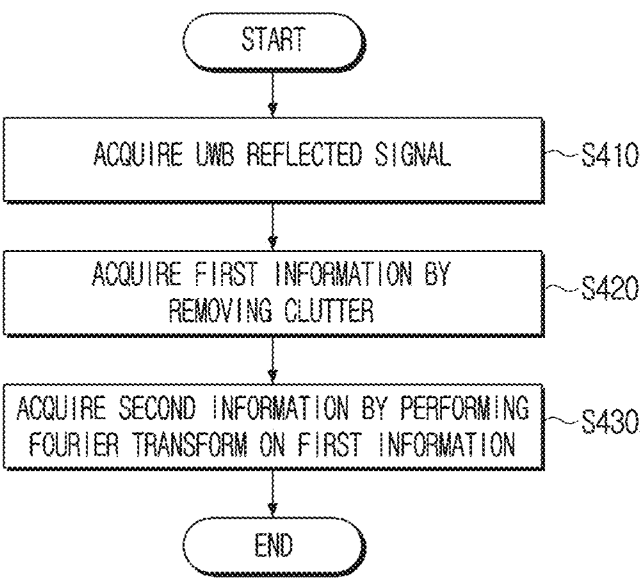
FIGS. 4A and 4B are views illustrating a method of acquiring information on a user's movement according to various embodiments of the disclosure.
Figure 4B:
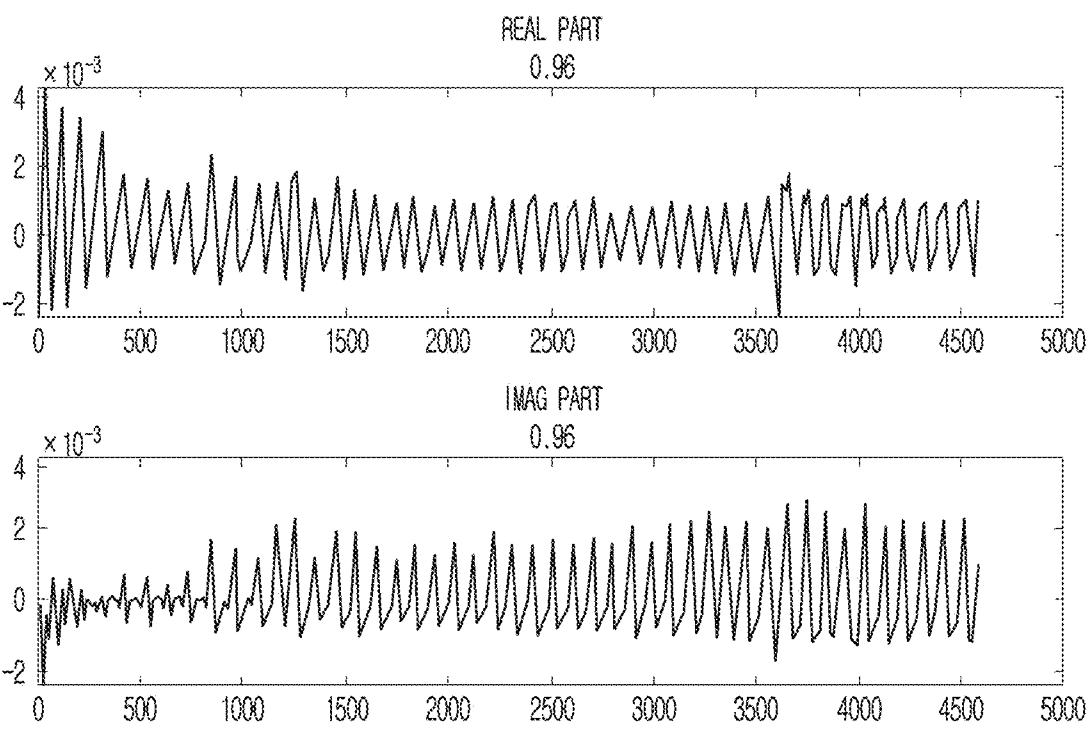

FIGS. 4A and 4B are views illustrating a method of acquiring information on a user's movement according to various embodiments of the disclosure.

Referring to FIG. 4A, a movement information acquisition module 161 may acquire information on the user's movement during sleep. The movement information acquisition module 161 may transmit a radar signal through a UWB radar sensor (e.g., UWB sensor 150) and receive the UWB signal 310 reflected by the user, at operation S410.

Referring to FIG. 4B, a movement information acquisition module 161 may acquire reflected UWB signal data.

When the reflected UWB signal data is acquired, the movement information acquisition module 161 may remove clutter from the reflected signal to acquire first information on the user's movement, at operation S420. The clutter may be a signal irrelevant to the user's movement, a signal in which no movement is detected for a predetermined time or more, or a noise signal. In other words, the reflected UWB signal may include a signal received after being reflected by various objects other than the user, that are, words, a background object such as a wall, a table, or a chair. Accordingly, the movement information acquisition module 161 may remove the clutter signal, which is a signal received by being reflected by an object other than the user.

Specifically, the movement information acquisition module 161 may remove clutter and acquire a signal for the user's movement by using a moving average method. In other words, the movement information acquisition module 161 may remove the clutter signal of the received UWB signal by using an average value of the acquired signals. The movement information acquisition module 161 may acquire a signal for the user's movement by removing clutter from the reflected signal, and acquire first information on the user's movement by accumulating the signal for the user's movement in chronological order.

The movement information acquisition module 161 may perform the Fourier transform on the first information to acquire second information on the user's movement, at operation S430. Specifically, the movement information acquisition module 161 may perform the Fourier transform (e.g., Short-time Fourier transform (SFFT)) on the first information in a moving window or sliding window method, and acquire second information on the frequency of the user's movement by accumulating a performance result of the Fourier transform in chronological order.

For example, the movement information acquisition module 161 may acquire a distance map of the user's movement, and may acquire a Doppler map by performing the Fourier transform on the distance map of the user's movement.

In addition, the sleep information acquisition module 162 may acquire information 360 on the user's sleep based on the first information 320 on the user's movement and the second information 330 on the user's movement.

Specifically, the sleep information acquisition module 162 may acquire first feature information 340 indicating the feature of the first information by inputting the first information 320 to a first neural network 111A, and second feature information 350 indicating the feature of the second information by inputting the second information 330 to a second neural network 111B.

In that configuration, the first neural network may include a Conv1d layer, a batch normalization layer, and a Squeeze and Excitation network (SENet) layer. Similarly, the second neural network may include a Conv1d layer, a batch normalization layer, and a Squeeze and Excitation network (SENet) layer.

Figure 5:
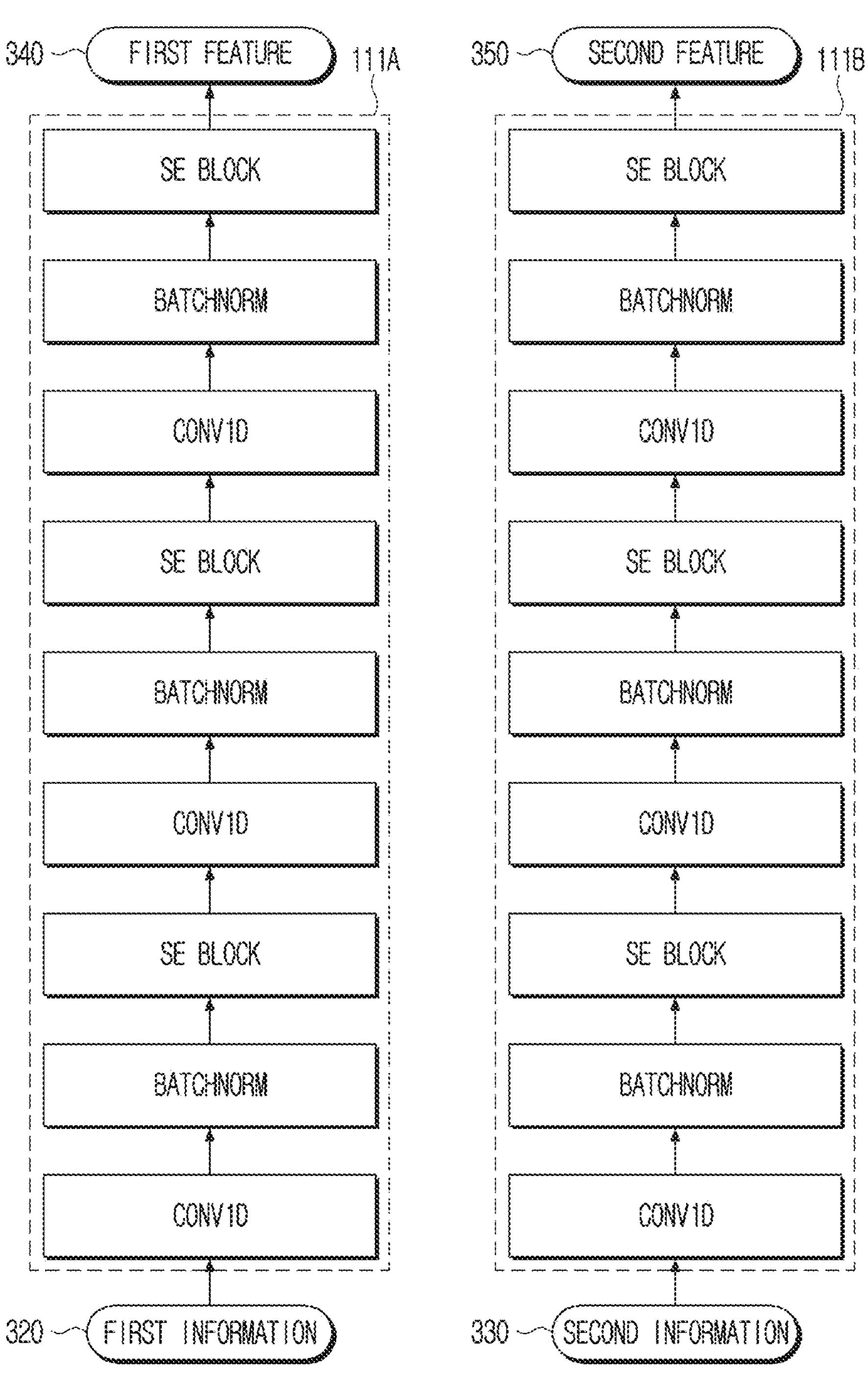
FIGS. 5 and 6 are views illustrating a first neural network, a second neural network, and a third neural network according to various embodiments of the disclosure.
Figure 6:
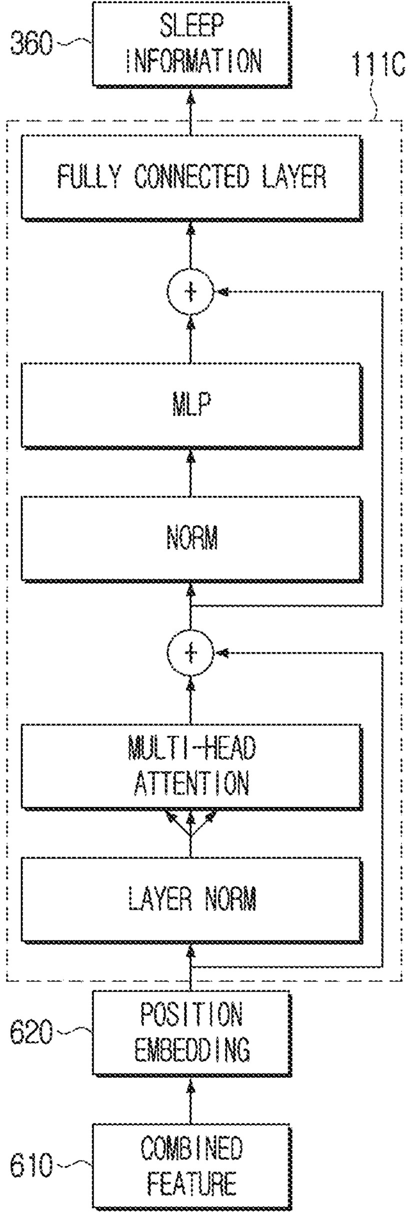

FIGS. 5 and 6 are views illustrating a first neural network, a second neural network, and a third neural network according to various embodiments of the disclosure.

Referring to FIG. 5, a first neural network 111A and the second neural network 111B may be implemented accordingly, for example.

In addition, the sleep information acquisition module 162 may acquire the information 360 on the user's sleep by inputting the first feature information 340 and the second feature information 350 into a third neural network 111C.

In that configuration, the third neural network 111C may include a Bidirectional-Long Short-Term Memory (Bi-LSTM) layer.

Alternatively, the third neural network 111C may include a Transformer network layer.

Referring to FIG. 6, a third neural network 111C may be implemented accordingly, for example.

In this configuration, the sleep information acquisition module 162 may acquire the information on the user's sleep by inputting the feature information 610 in which the first feature information 340 and the second feature information 350 are combined into the third neural network 111C. In this configuration, the sleep information acquisition module 162 may input data acquired by performing position embedding 620 on the feature information combining the first feature information 340 and the second feature information 350 into the third neural network 111C. In this configuration, the sleep information acquisition module 162 may flatten a patch of information in which the first feature information 340 and the second feature information 350 are combined, and input data acquired by performing position embedding to the combined information into the third neural network 111C without inputting a dimensional vectorized data into the third neural network 111C, thereby improving the performance of the artificial intelligence model 111. The sleep information acquisition module 162 may combine the first feature information 340 and the second feature information 350 through various feature fusion methods. Specifically, the sleep information acquisition module 162 may combine the first feature information 340 and the second feature information 350 in a concatenation method of accumulating and summing the first feature information 340 and the second feature information 350.

Alternatively, the sleep information acquisition module 162 may combine the first feature information 340 and the second feature information 350 by multiplying the first feature information 340 and the second feature information 350 for each element (Element-wise Multiply).

Alternatively, the sleep information acquisition module 162 may combine the first feature information 440 and the second feature information 350 in a bi-directional feature pyramid network (BiFPN) method. In that configuration, the sleep information acquisition module 162 may combine the first feature information 340 and the second feature information 350 through Equation 1 below.

$$Y=(W1X1+W2X2/W1)/(W1+W2+e) \qquad \text{Equation 1}$$

In that configuration, Y may represent combined feature, X1 may represent the first feature information 340, X2 may represent the second feature information 350, and W1, W2, and e may represent arbitrary weights or constants.

Meanwhile, a method for the sleep information acquisition module 162 to combine the first feature information 340 and the second feature information 350 is not limited to the method described above, and the first feature information 340 and the second feature information may be combined through various combining methods such as element-wise add of the first feature information 340 and the second feature information 350.

In addition, the performance of the artificial intelligence model 111 may vary according to a method of combining a type of input data input to the artificial intelligence model 111, a measurement time of learning data, a neural network structure of the artificial intelligence model 111, and a method of combining the first feature information 440 and the second feature information 450.

FIG. 7 is a view illustrating a performance of an artificial intelligence model according to an embodiment of the disclosure.

Referring to FIG. 7, accuracy, sensitivity, and specificity of an artificial intelligence model 111 may be different according to the type of input data, the measurement time of the learning data, the neural network structure, and the method of combining feature information.

In that configuration, 1DCNN-LSTM structure among the neural network structures of the artificial intelligence model 111 may be a 1DCNN-LSTM structure in which 1DCNN layer and LSTM layer are combined. In addition, two-stream 1DCNN-LSTM structure may be a structure in which two 1DCNN-LSTM layers for respectively outputting the first feature information 340 and the second feature information 350 are implemented. In addition, the two-stream 1DCNN-SENet-Transformer Network structure may have a structure including two 1DCNN-SENet layers for outputting the first information 320 and the second information 330, and a Transformer Network layer for receiving the first feature information 340 and the second feature information 350.

There may be a concatenation, element-wise multiply, or Bifpn method for combining the first feature information 340 and the second feature information 350 of the artificial intelligence model 111.

In this configuration, referring to the data of a first row 710 and a second row 720 of FIG. 7, as a measurement time of learning data increases from 10 minutes to 60 minutes, accuracy of the artificial intelligence model 111 increases from 0.785 to 0.817.

Referring to data of a third row 730 and a fourth row 740, when only the first information 320 on the user's movement is input to the artificial intelligence model 111, accuracy of the artificial intelligence model 111 is 0.817, and when only the second information 330 is input to the artificial intelligence model 111, accuracy of the artificial intelligence model 111 is 0.891. Meanwhile, when the first information 320 and the second information 330 are input to the intelligence model 111, accuracy of the artificial intelligence model increases to 0.907.

In addition, referring to data of the fourth row 740 and a fifth row 750, when a neural network structure of the artificial intelligence model 111 is a Two-stream 1DCNN-SENet-Transformer Network structure rather than a Two-stream 1DCNN-SENet, accuracy of the artificial intelligence model 111 increases from 0.907 to 0.927 and specificity thereof is maintained, while sensitivity increases from 0.78 to 0.816.

According to an embodiment of the disclosure, the sleep information acquisition module 162 may acquire information on the apnea-hypopnea index per hour for the user's total sleep time based on information on the user's movements accumulated during the user's total sleep time.

Specifically, the sleep information acquisition module 162 may acquire information on sleep for each time in a sliding window method using information accumulated during the user's total sleep time.

For example, the sleep information acquisition module 162 may acquire information on the user's apnea-hypopnea index for each time interval based on a time interval such as 1:00 to 2:00, 1:10 to 2:10, and 1:20 to 2:20 of the total sleep time.

Figure 8:
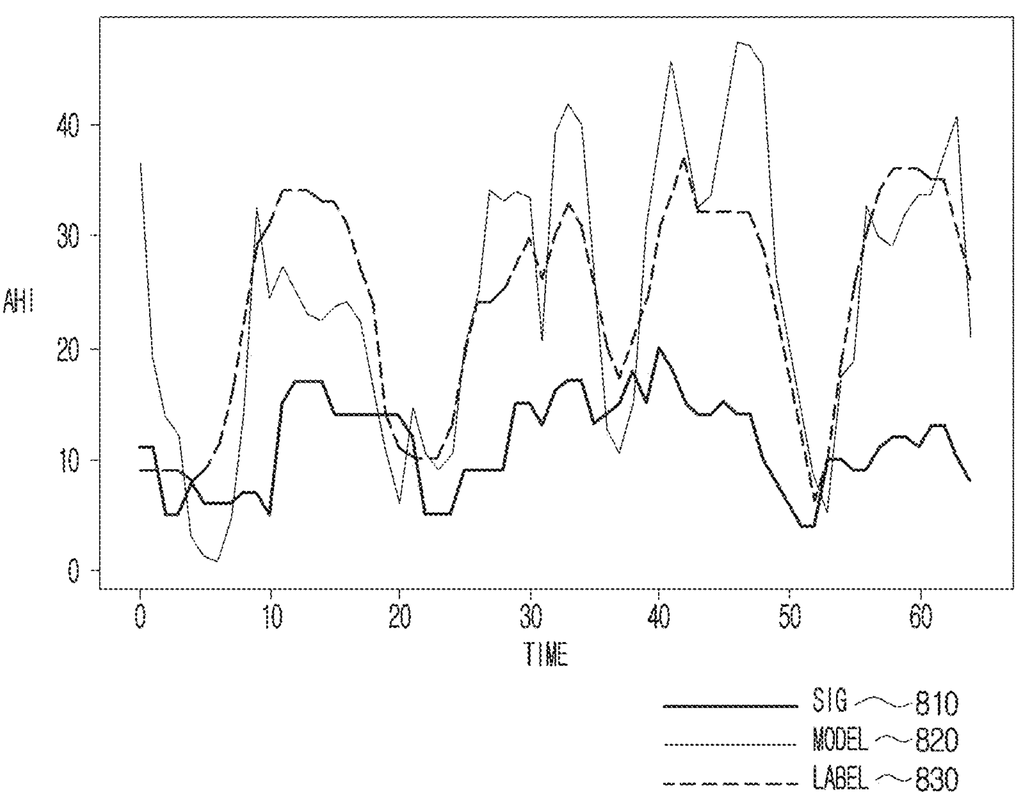
FIG. 8 is a view illustrating a method for an electronic apparatus to acquire information on sleep for each time during a user's sleep according to an embodiment of the disclosure.

FIG. 8 is a view illustrating the user's apnea-hypopnea index as time passes based on the user's movement information accumulated from 1:00 to 2:00 in a sleep information acquisition module according to an embodiment of the disclosure.

In this configuration, a user with severe sleep apnea may have apnea symptoms in most time intervals rather than a specific time interval, and based on this information, the sleep information acquisition module 162 may identify a degree of sleep apnea of the user.

Meanwhile, it may be identified that the user's apnea-hypopnea index 820 identified using the artificial intelligence model 111 is similar to an actual labeled data 830. Without using the artificial intelligence model 111, the user's apnea-hypopnea index 810 identified using only the UWB signal may have a large error with the actual labeled data 830.

In addition, when the information 360 on the user's sleep is acquired, the information providing module 163 may provide information on the user's sleep apnea or hypopnea. Specifically, the information providing module 163 may control the display 140 to display the user's sleep apnea or hypopnea diagnosis result. For example, the information providing module 163 may provide information on a degree (e.g., mild, moderate, or severe) of the user's sleep apnea together with the user's AHI index information.

Alternatively, when it is identified that the user's sleep apnea-hypopnea index is equal to or greater than a predetermined value, the information providing module 163 may control the display 140 to provide medical treatment information to the user. In that configuration, the medical treatment information may be information necessary for the user to receive hospital treatment.

For example, the information providing module 163 may identify a location of the electronic apparatus 100 through a global positioning system (GPS) sensor (not shown), and control the display 140 to provide a hospital that can provide treatment for sleep apnea located within a certain range from the location of the electronic apparatus 100.

Meanwhile, the artificial intelligence model 111 according to an embodiment of the disclosure may be a model learned based on sleep test data of the user other than the user of the electronic apparatus 100. Accordingly, the personalization module 164 may update the artificial intelligence model 111 to a personalized (or optimized) artificial intelligence model for the user of the electronic apparatus 100.

The personalization module 164 may update the artificial intelligence model 111 by using information acquired from the user of the electronic apparatus 100.

Specifically, the personalization module 164 may update parameters of the first neural network or the second neural network by inputting the first information on the user's movement or the second information on the user's movement into a fourth neural network stored in the memory 110.

In that configuration, the fourth neural network may be implemented in a form of an auto encoder including an encoder layer and a decoder layer. The auto-encoder may be a neural network for outputting data similar to input data. Here, the encoder layer may correspond to the first neural network or the second neural network. In other words, when the first information or the second information is input, the encoder layer may output the first feature information corresponding to the first information or the second feature information corresponding to the second information. In addition, when the first feature information or the second feature information is input, the decoder layer may output restored first information or restored second information. In other words, the input data of the fourth neural network may be the first information or the second information, and the output data of the fourth neural network may be the restored first information or the restored second information.

Figure 9:
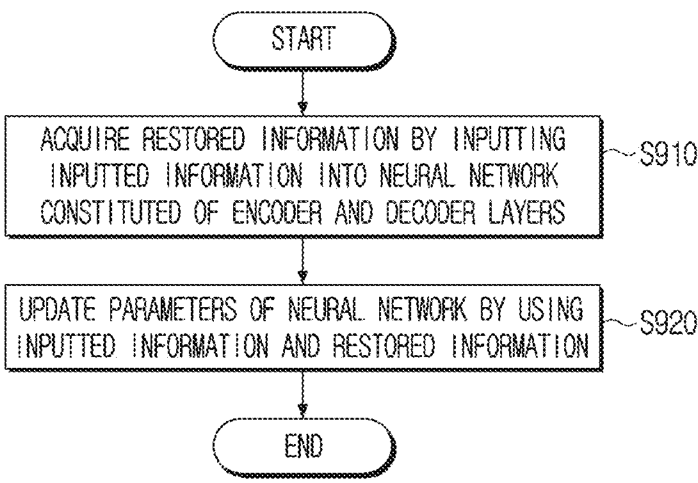
FIG. 9 is a view illustrating a method of personalizing an artificial intelligence model according to an embodiment of the disclosure.

FIG. 9 is a view illustrating a method of personalizing an artificial intelligence model according to an embodiment of the disclosure.

Referring to FIG. 9, a personalization module 164 may acquire the restored first information or the restored second information by inputting the first information or the second information into the fourth neural network, at operation S910.

The personalization module 164 may update parameters of each layer of the auto-encoder by comparing the input data and output data of the fourth neural network, at operation S920. Specifically, the personalization module 164 may calculate an error by comparing input data and output data of the fourth neural network, and back-propagate the calculated error in the fourth neural network, and update a parameter (or connection weight) of each node of each layer according to the back-propagation.

The personalization module 164 may update parameters of the first neural network or the second neural network by using the updated parameters of the encoder layer of the fourth neural network at operation S930.

Through the method described above, the personalization module 164 may minimize a difference (environmental difference, user difference) between learning data and test data of the artificial intelligence model 111, and update by optimizing the artificial intelligence model 111 for user of the electronic apparatus 100.

Meanwhile, the artificial intelligence model 111, the first neural network 111A, the second neural network 112B, or the third neural network 111C according to the disclosure may be stored in the memory 110, but this is only an embodiment, and may be stored in an external server. In that configuration, the electronic apparatus 100 may communicate with an external device (e.g., a server) and perform an operation for acquiring information on the user's sleep.

Figure 10:
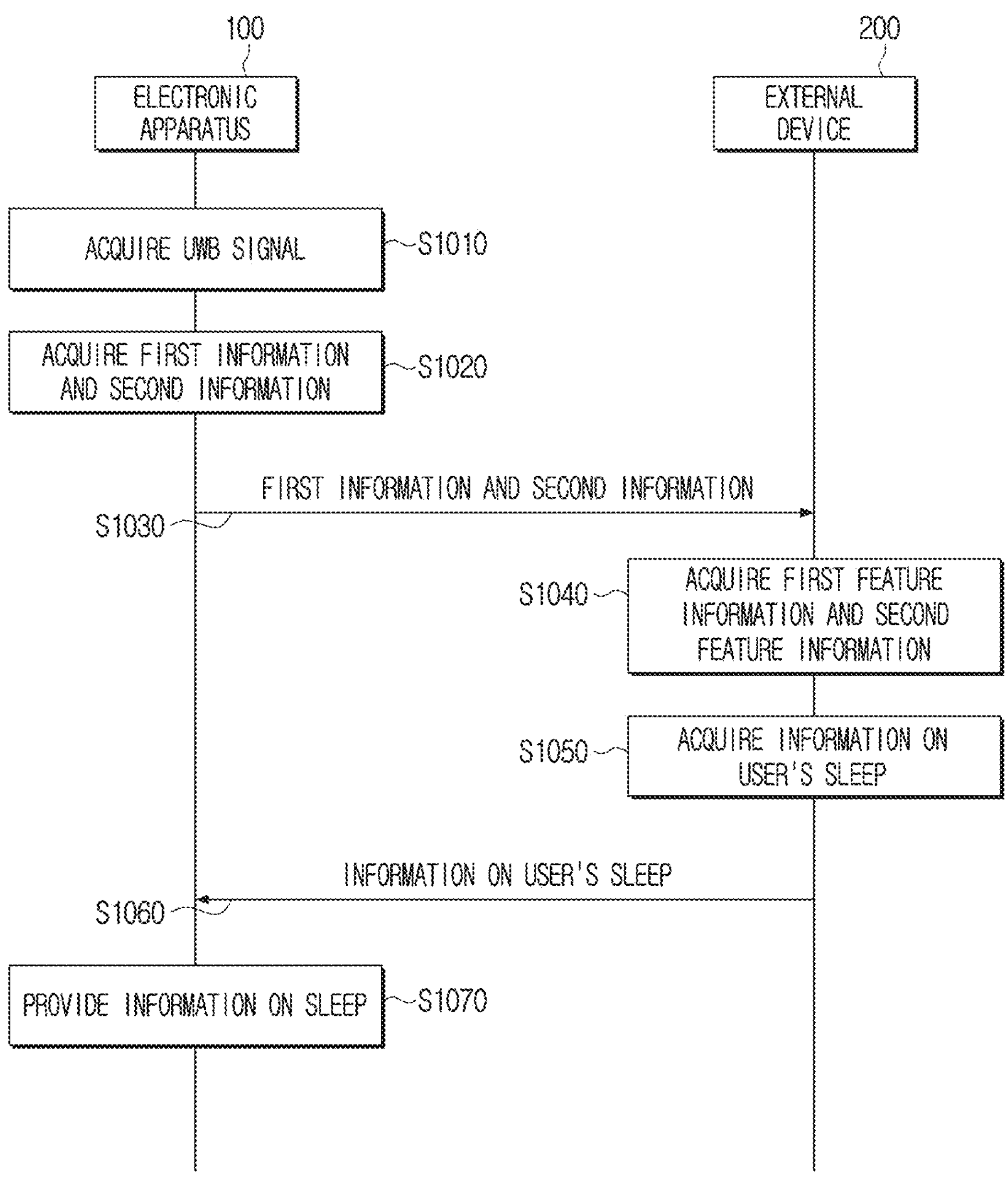
FIG. 10 is a view illustrating a method for an electronic apparatus to acquire information on a user's sleep while communicating with an external server according to an embodiment of the disclosure.

FIG. 10 is a view illustrating a method for an electronic apparatus to acquire information on a user's sleep while communicating with an external server according to an embodiment of the disclosure.

Referring to FIG. 10, an electronic apparatus 100 may acquire a UWB signal using the UWB sensor 150, at operation S1010.

The electronic apparatus 100 may acquire first information on the user's movement by removing clutter from the acquired UWB signal, and may acquire second information by performing a Fourier transform on the first information, at operation S1020.

When the first information and the second information are acquired, the electronic apparatus 100 may transmit the first information and the second information to an external device 200 through the communication interface 120, at operation S1030.

The external device 200 may acquire the first feature information and the second feature information by inputting the transmitted first information and the second information to the first neural network and the second neural network, at operation S1040.

The external device 200 may acquire information on the user's sleep by inputting the acquired first feature information and the second feature information to the third neural network, at operation S1050.

When information on the user's sleep is acquired, the external device 200 may transmit information on the user's sleep to the electronic apparatus 100, at operation S1060.

When information on the user's sleep is received, the electronic apparatus 100 may provide information on the user's sleep, at operation S1070.

Figure 11:
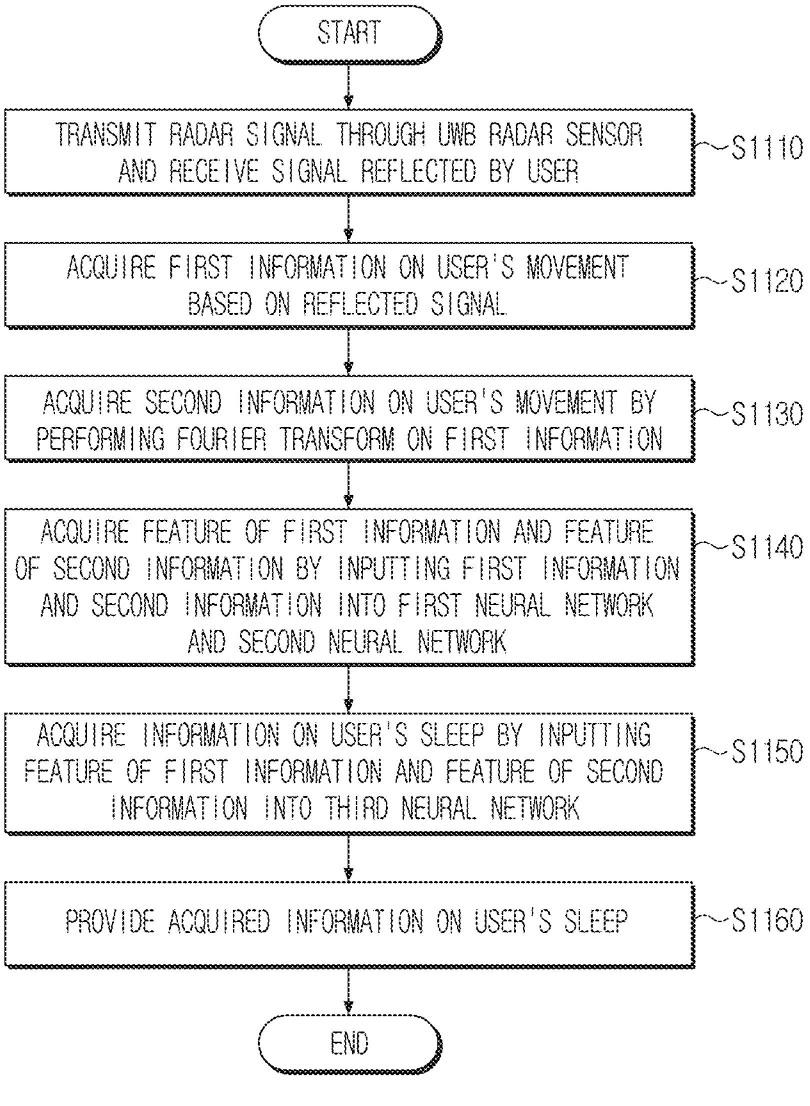
FIG. 11 is a view illustrating a method of controlling an electronic apparatus according to an embodiment of the disclosure.

FIG. 11 is a view illustrating a method of controlling an electronic apparatus according to an embodiment of the disclosure.

Referring to FIG. 11, an electronic apparatus 100 may transmit a radar signal through the UWB radar sensor and receive a signal reflected by the user, at operation S1110.

The electronic apparatus 100 may acquire first information on the user's movement based on the reflected signal, at operation S1120. Specifically, the electronic apparatus 100 may acquire the first information by removing clutter from the reflected signal.

The electronic apparatus 100 may acquire second information on the user's movement by performing a Fourier transform on the first information, at operation S1130.

The electronic apparatus 100 may acquire the feature information of the first information and the feature information of the second information by inputting the first information and the second information to the first neural network and the second neural network, respectively, at operation S1140. In that configuration, the first neural network and the second neural network may include a 1DCNN layer and an SENet layer for outputting the first feature information and the second feature information.

The electronic apparatus 100 may acquire information on the user's sleep by inputting the feature of the first information and the feature of the second information into the third neural network, at operation S1150. In that configuration, the information on the user's sleep may be information on the user's apnea or hypopnea during sleep.

The electronic apparatus 100 may provide information on the acquired sleep, at operation S1160. Specifically, the electronic apparatus 100 may control the display 140 to display information on the acquired sleep.

The term "module" as used herein includes units made up of hardware, software, or firmware, and may be used interchangeably with terms such as logic, logic blocks, components, or circuits. A "module" may be an integrally constructed component or a minimum unit or part thereof that performs one or more functions. For example, the module may be configured as an application-specific integrated circuit (ASIC).

According to an embodiment, the various embodiments described above may be implemented as software including instructions stored in a machine-readable storage media which is readable by a machine (e.g., a computer). The device may include the electronic apparatus 100 according to the disclosed embodiments, as a device which calls the stored instructions from the storage media and which is operable according to the called instructions. When the instructions are executed by a processor, the processor may directory perform functions corresponding to the instructions using other components or the functions may be performed under a control of the processor. The instructions may include a code made by a compiler or a code executable by an interpreter. The machine-readable storage media may be provided in a form of a non-transitory storage media. Herein, the term "non-transitory" only denotes that a storage medium does not include a signal but is tangible, and does not distinguish the case where a data is semi-permanently stored in a storage medium from the case where a data is temporarily stored in a storage medium.

In addition, according to an embodiment, the methods according to various embodiments described above may be provided as a part of a computer program product. The computer program product may be traded between a seller and a buyer. The computer program product may be distributed online in the form of machine-readable storage media (e.g., compact disc read only memory (CD-ROM)) or through an application store (e.g., Play Store™). In the case of online distribution, at least a portion of the computer program product may be at least temporarily stored or temporarily generated in a server of the manufacturer, a server of the application store, or a storage medium such as memory.

The respective components (e.g., module or program) according to the various example embodiments may include a single entity or a plurality of entities, and some of the corresponding sub-components described above may be omitted, or another sub-component may be further added to the various example embodiments. Alternatively or additionally, some components (e.g., module or program) may be combined to form a single entity which performs the same or similar functions as the corresponding elements before being combined. Operations performed by a module, a program, or other component, according to various embodiments, may be sequential, parallel, or both, executed iteratively or heuristically, or at least some operations may be performed in a different order, omitted, or other operations may be added.

While the disclosure has been shown and described with reference to various embodiments thereof, it will be understood by those skilled in the art that various changes in form and details may be made therein without departing from the spirit and scope of the disclosure as defined by the appended claims and their equivalents.

What is claimed is:

1. An electronic apparatus comprising:

an ultra-wideband (UWB) sensor;

memory storing at least one instruction; and a processor connected to the memory, wherein, the instructions, when executed by the processor, cause the electronic apparatus to:

transmit a radar signal through the UWB sensor and receive a signal reflected by a user, based on the signal reflected by the user, acquire first information on a user's movement, acquire second information on the user's movement by performing a Fourier transform on the first information, acquire first feature information corresponding to the first information by inputting the first information into a first neural network, acquire second feature information corresponding to the second information by inputting the second information into a second neural network, acquire input data acquired by performing position embedding on feature information combining element-wise the first feature information and the second feature information, acquire sleep information on a user's sleep by inputting the input data into a third neural network, and provide the sleep information on the user's sleep, wherein the first information includes a distance map with respect to a movement of a user's chest, and the second information includes a Doppler map with respect to the movement of the user's chest, and wherein the instructions, when executed by the processor, further cause the electronic apparatus to:

acquire the sleep information on the user's sleep by inputting a value acquired by multiplying the first feature information and the second feature information for each element into the third neural network.

2. The electronic apparatus of claim 1, wherein the first information includes time series information on the user's movement according to a change of time, and wherein the second information includes time series information on a frequency of the user's movement according to the change of time.

3. The electronic apparatus of claim 1, wherein the first neural network includes a convolutional neural network (CNN) for outputting the first feature information, and wherein the instructions, when executed by the processor, further cause the electronic apparatus to:

acquire restored first information using the first feature information, and train parameters of the CNN by comparing the restored first information with the first information.

4. The electronic apparatus of claim 1, wherein the second neural network includes a convolutional neural network (CNN) for outputting the second feature information, and wherein the instructions, when executed by the processor, further cause the electronic apparatus to:

acquire restored second information by using the second feature information, and train parameters of the CNN by comparing the restored second information with the second information.

5. The electronic apparatus of claim 1, wherein the instructions, when executed by the processor, further cause the electronic apparatus to:

train the first neural network, the second neural network, and the third neural network based on movement information on the user's movement measured over a predetermined time.

6. A method of controlling an electronic apparatus, the method comprising:

transmitting a radar signal through an ultra-wideband (UWB) sensor and receiving a signal reflected by a user;

based on the signal reflected by the user, acquiring first information on a user's movement;

acquiring second information on the user's movement by performing a Fourier transform on the first information;

acquiring first feature information corresponding to the first information by inputting the first information into a first neural network;

acquiring second feature information corresponding to the second information by inputting the second information into a second neural network;

acquiring input data acquired by performing position embedding on feature information combining element-wise the first feature information and the second feature information;

acquiring sleep information on a user's sleep by inputting the input data into a third neural network; and providing the sleep information on the user's sleep, wherein the first information includes a distance map with respect to a movement of a user's chest, and the second information includes a Doppler map with respect to the movement of the user's chest, and wherein the acquiring of the sleep information on the user's sleep comprises acquiring the sleep information on the user's sleep by inputting a value acquired by multiplying the first feature information and the second feature information for each element into the third neural network.

7. The method of claim 6, wherein the first information includes time series information on the user's movement according to a change of time, and wherein the second information includes time series information on a frequency of the user's movement according to the change of time.

8. The method of claim 6, wherein the first neural network includes a convolutional neural network (CNN) for outputting the first feature information, and wherein the method further comprises:

acquiring restored first information using the first feature information; and training parameters of the CNN by comparing the restored first information with the first information.

9. The method of claim 6, wherein the second neural network includes a convolutional neural network (CNN) for outputting the second feature information, and wherein the method further comprises:

acquiring restored second information by using the second feature information; and training parameters of the CNN by comparing the restored second information with the second information.

10. The method of claim 6, further comprising:

training the first neural network, the second neural network, and the third neural network based on movement information on the user's movement measured over a predetermined time.

11. The method of claim 6, wherein the first neural network, the second neural network, and the third neural network have a structure of a two stream one dimensional convolution neural network (1DCNN)-squeeze and excitation network (SENet)-transformer network.

12. The method of claim 6, further comprising updating at least one of the first neural network or the second neural network by inputting a corresponding one of the first information or the second information into a fourth neural network.

13. One or more non-transitory computer-readable storage media storing one or more computer programs including instructions that, when executed by a processor of an electronic apparatus, cause the electronic apparatus to perform operations, the operations comprising:

transmitting a radar signal through an ultra-wideband (UWB) sensor and receiving a signal reflected by a user;

based on the signal reflected by the user, acquiring first information on a user's movement;

acquiring second information on the user's movement by performing a Fourier transform on the first information;

acquiring first feature information corresponding to the first information by inputting the first feature information into a first neural network;

acquiring second feature information corresponding to the second information by inputting the second information into a second neural network;

acquiring input data acquired by performing position embedding on feature information combining element-wise the first feature information and the second feature information;

acquiring sleep information on a user's sleep by inputting the input data into a third neural network; and providing the sleep information on the user's sleep, wherein the first information includes a distance map with respect to a movement of a user's chest, and the second information includes a Doppler map with respect to the movement of the user's chest, and wherein the acquiring of the sleep information on the user's sleep comprises acquiring the sleep information on the user's sleep by inputting a value acquired by multiplying the first feature information and the second feature information for each element into the third neural network.

14. The one or more non-transitory computer-readable storage media of claim 13, wherein the acquiring of the sleep information includes inputting data, which is acquired by performing position embedding on feature information combining the first feature information and the second feature information, into the third neural network.

15. The one or more non-transitory computer-readable storage media of claim 13, wherein the first neural network includes a first Conv1d layer, a first batch normalization layer, and a first Squeeze and Excitation network (SENet) layer, wherein the second neural network includes a second Conv1d layer, a second batch normalization layer, and a second SENet layer, and wherein the third neural network includes at least one of a Bidirectional-Long Short-Term Memory (Bi-LSTM) layer or a Transformer network layer.

16. The one or more non-transitory computer-readable storage media claim 13, wherein, in providing the sleep information on the user's sleep, the operations further comprise:

in response to acquiring the sleep information, displaying a user's sleep apnea or hypopnea diagnosis result, which includes information on one of a mild degree, a moderate degree, or a severe degree of the user's sleep apnea or hypopnea, together with a user's Apnea-Hypopnea Index (AHI) index information.

* * * * *